(12) United States Patent
McArthur et al.

(10) Patent No.: US 9,751,056 B2
(45) Date of Patent: Sep. 5, 2017

(54) MIXING SYRINGE

(71) Applicants: Merit Medical Systems, Inc., South Jordan, UT (US); IKOMED Technologies, Inc., Vancouver (CA)

(72) Inventors: Gregory R. McArthur, Sandy, UT (US); Lindsay S. Machan, Vancouver (CA); Daniel Gelbart, Vancouver (CA)

(73) Assignees: Merit Medical Systems, Inc., South Jordan, UT (US); IKOMED Technologies, Inc., Vancouver (CA)

( * ) Notice: Subject to any disclaimer, the term of this patent is extended or adjusted under 35 U.S.C. 154(b) by 322 days.

(21) Appl. No.: 14/283,901

(22) Filed: May 21, 2014

(65) Prior Publication Data

US 2014/0254303 A1    Sep. 11, 2014

Related U.S. Application Data

(63) Continuation-in-part of application No. PCT/US2013/022561, filed on Jan. 22, 2013, which
(Continued)

(51) Int. Cl.
   B01F 5/06 (2006.01)
   B01F 13/00 (2006.01)
   (Continued)

(52) U.S. Cl.
   CPC ....... B01F 13/0023 (2013.01); A61M 5/3145 (2013.01); A61M 5/31596 (2013.01); B01F 5/0608 (2013.01); A61M 2005/31516 (2013.01)

(58) Field of Classification Search
   CPC .... A61M 2005/31516; A61M 5/31596; A61M 5/3145; B01F 13/0023; B01F 5/0608
   See application file for complete search history.

(56) References Cited

U.S. PATENT DOCUMENTS 2,514,454 A   7/1950  Nicholson
3,493,503 A   2/1970  Mass
(Continued)

FOREIGN PATENT DOCUMENTS

CN   101732781   6/2010
DE   10356335    6/2005
(Continued)

OTHER PUBLICATIONS

Notice of Allowance dated Jun. 4, 2014 for U.S. Appl. No. 13/385,627.
(Continued)

*Primary Examiner* — Quynh-Nhu H Vu
(74) *Attorney, Agent, or Firm* — Stoel Rives LLP

(57) ABSTRACT

A movable mixing disc may be utilized in connection with a syringe. The mixing disc may comprise a hole which may be covered by a fine screen or coupled to a porous member, allowing only certain elements of a solution to pass through the mixing disc. Actuation of a plunger of the syringe may cause liquid to emerge from the mixing disc hole as a high velocity jet or other turbulent flow, stirring up any settled particles on a distal side of the mixing disc. As the ejection continues, the mixing disc may be pushed forward by the plunger in order to eliminate any unused volume. Also, the mixing disc may be moved forward by virtue of a pressure difference created by a pressure drop across the mixing disc, such as a pressure drop created as the plunger is displaced to induce fluid flow across the mixing disc.

12 Claims, 10 Drawing Sheets

Related U.S. Application Data is a continuation-in-part of application No. 13/385,627, filed on Feb. 28, 2012, now Pat. No. 8,834,449.

(60) Provisional application No. 61/632,263, filed on Jan. 23, 2012.

(51) Int. Cl.
  *A61M 5/31* (2006.01)
  *A61M 5/315* (2006.01)

(56) References Cited

U.S. PATENT DOCUMENTS

| | | | |
|---|---|---|---|
| 3,548,825 A | 12/1970 | Shaw | |
| 3,570,486 A | 3/1971 | Engelsher et al. | |
| 3,606,094 A | 9/1971 | Mills et al. | |
| 3,661,265 A | 5/1972 | Greenspan | |
| 3,680,558 A * | 8/1972 | Kapelowitz | A61B 5/1416 |
| | | | 604/89 |
| 3,724,077 A | 4/1973 | Preston et al. | |
| 3,838,659 A * | 10/1974 | Coleman, II | E02B 3/24 |
| | | | 114/218 |
| 3,838,689 A * | 10/1974 | Cohen | A61M 5/31596 |
| | | | 604/90 |
| 3,889,674 A | 6/1975 | Cilento | |
| 3,938,513 A * | 2/1976 | Hargest | A61M 5/3145 |
| | | | 604/190 |
| 4,031,892 A | 6/1977 | Hurschman | |
| 4,041,945 A | 8/1977 | Guiney | |
| 4,116,240 A | 9/1978 | Guiney | |
| 4,412,836 A | 11/1983 | Brignola | |
| 4,435,507 A | 3/1984 | Stenkvist | |
| 4,437,858 A | 3/1984 | Ty | |
| 4,698,299 A | 10/1987 | Janoff et al. | |
| 4,722,792 A * | 2/1988 | Miyagi | B01D 33/11 |
| | | | 210/360.1 |
| 4,751,921 A | 6/1988 | Park | |
| 4,776,704 A | 10/1988 | Kopunek et al. | |
| 4,820,276 A * | 4/1989 | Moreno | A61M 5/3145 |
| | | | 222/189.06 |
| 4,981,468 A | 1/1991 | Benefiel et al. | |
| 5,002,537 A | 3/1991 | Hoffman et al. | |
| 5,069,670 A | 12/1991 | Vetter et al. | |
| 5,122,117 A | 6/1992 | Haber et al. | |
| 5,139,490 A | 8/1992 | Vetter et al. | |
| 5,244,465 A | 9/1993 | Michel | |
| 5,298,023 A | 3/1994 | Haber et al. | |
| 5,308,340 A | 5/1994 | Harris | |
| 5,320,603 A | 6/1994 | Vetter et al. | |
| 5,360,410 A | 11/1994 | Wacks | |
| 5,372,029 A | 12/1994 | Brandes | |
| 5,435,076 A | 7/1995 | Hjertman et al. | |
| 5,501,673 A | 3/1996 | Hjertman et al. | |
| 5,514,097 A | 5/1996 | Knauer | |
| 5,542,411 A | 8/1996 | Rex | |
| 5,549,561 A | 8/1996 | Hjertman | |
| 5,549,575 A | 8/1996 | Giambattista et al. | |
| 5,554,134 A | 9/1996 | Bonnichsen | |
| 5,592,866 A | 1/1997 | Sher | |
| 5,626,566 A | 5/1997 | Petersen et al. | |
| 5,660,205 A * | 8/1997 | Epstein | A61M 39/24 |
| | | | 137/512.15 |
| 5,685,846 A * | 11/1997 | Michaels, Jr. | A61M 5/31596 |
| | | | 604/181 |
| 5,693,027 A | 12/1997 | Hansen et al. | |
| 5,716,338 A | 2/1998 | Hjertman et al. | |
| 5,725,500 A | 3/1998 | Micheler | |
| 5,725,508 A | 3/1998 | Chanoch et al. | |
| 5,785,682 A | 7/1998 | Grabenkort | |
| 5,785,692 A | 7/1998 | Attermeier et al. | |
| 5,788,670 A | 8/1998 | Reinhard et al. | |
| 5,817,056 A * | 10/1998 | Tanaka | A61M 5/284 |
| | | | 604/84 |
| 5,820,602 A | 10/1998 | Kovelman et al. | |
| 5,823,998 A | 10/1998 | Yamagata | |
| 5,876,372 A * | 3/1999 | Grabenkort | A61M 5/31596 |
| | | | 604/89 |
| 5,891,087 A | 4/1999 | Ohtani et al. | |
| 6,036,675 A | 3/2000 | Thorne et al. | |
| 6,106,501 A | 8/2000 | Michel | |
| 6,126,646 A | 10/2000 | Hansen et al. | |
| 6,203,529 B1 | 3/2001 | Gabriel et al. | |
| 6,221,655 B1 * | 4/2001 | Fung | B01L 3/5021 |
| | | | 422/504 |
| 6,241,709 B1 | 6/2001 | Bechtold et al. | |
| 6,277,097 B1 | 8/2001 | Mikkelsen et al. | |
| 6,319,225 B1 | 11/2001 | Sugita et al. | |
| 6,331,173 B1 | 12/2001 | Ljungquist | |
| 6,419,656 B1 | 7/2002 | Vetter et al. | |
| 6,582,404 B1 | 6/2003 | Klitgaard et al. | |
| 6,582,408 B1 | 6/2003 | Buch-Rasmussen et al. | |
| 6,645,179 B1 | 11/2003 | Ishikawa et al. | |
| 6,679,248 B2 | 1/2004 | Stadelhofer | |
| 6,793,646 B1 | 9/2004 | Giambattista et al. | |
| 6,817,987 B2 | 11/2004 | Vetter et al. | |
| 6,878,338 B2 * | 4/2005 | Taylor | A61M 5/286 |
| | | | 422/430 |
| 6,899,698 B2 | 5/2005 | Sams | |
| 6,997,910 B2 * | 2/2006 | Howlett | A61M 5/284 |
| | | | 604/191 |
| 7,081,108 B2 | 7/2006 | Langley et al. | |
| 7,101,354 B2 | 9/2006 | Thorne et al. | |
| 7,402,150 B2 | 7/2008 | Matsumoto et al. | |
| 7,686,782 B2 | 3/2010 | Kirchhofer et al. | |
| 7,749,200 B2 | 7/2010 | Graf et al. | |
| 7,771,398 B2 | 8/2010 | Knight et al. | |
| 7,811,263 B2 | 10/2010 | Burren et al. | |
| 7,815,598 B2 | 10/2010 | Hommann et al. | |
| RE41,956 E | 11/2010 | Klitgaard et al. | |
| 7,828,172 B2 | 11/2010 | Stradella et al. | |
| 7,850,662 B2 | 12/2010 | Veasey et al. | |
| 7,867,202 B2 | 1/2011 | Moser et al. | |
| 7,883,490 B2 | 2/2011 | Casey, II et al. | |
| 7,918,832 B2 | 4/2011 | Veasey et al. | |
| 7,918,833 B2 | 4/2011 | Veasey | |
| 7,967,779 B2 | 6/2011 | Bertron et al. | |
| 8,002,734 B2 | 8/2011 | Bassarab et al. | |
| 8,075,515 B2 | 12/2011 | Matusch | |
| 8,075,517 B2 | 12/2011 | Karlsson et al. | |
| 8,092,421 B2 | 1/2012 | Seiferlein et al. | |
| 8,092,422 B2 | 1/2012 | Seiferlein et al. | |
| 8,096,971 B2 | 1/2012 | Bassarab et al. | |
| 8,152,766 B2 | 4/2012 | Karlsson et al. | |
| 8,187,233 B2 | 5/2012 | Harms et al. | |
| 8,246,577 B2 | 8/2012 | Schrul et al. | |
| 8,267,900 B2 | 9/2012 | Harms et al. | |
| 8,298,175 B2 | 10/2012 | Hirschel et al. | |
| 8,366,680 B2 | 2/2013 | Raab | |
| 8,376,993 B2 | 2/2013 | Cox et al. | |
| 8,398,593 B2 | 3/2013 | Eich et al. | |
| 8,414,541 B2 | 4/2013 | Spofforth | |
| 8,439,864 B2 | 5/2013 | Galbraith et al. | |
| 8,834,449 B2 * | 9/2014 | Machan | A61M 5/31596 |
| | | | 604/518 |
| 2001/0007062 A1 * | 7/2001 | Dumaresq-Lucas | A61M 5/3145 |
| | | | 604/236 |
| 2001/0053894 A1 | 12/2001 | Steenfeldt-Jensen et al. | |
| 2002/0033367 A1 | 3/2002 | Prince et al. | |
| 2002/0165500 A1 | 11/2002 | Bechtold et al. | |
| 2002/0173752 A1 | 11/2002 | Polzin | |
| 2003/0032935 A1 | 2/2003 | Damiano et al. | |
| 2003/0036724 A1 | 2/2003 | Vetter et al. | |
| 2004/0092883 A1 | 5/2004 | Casey, II et al. | |
| 2004/0108339 A1 | 6/2004 | Hansen et al. | |
| 2004/0158226 A1 * | 8/2004 | Soo Hoo | C12M 23/34 |
| | | | 604/500 |
| 2004/0186441 A1 | 9/2004 | Graf et al. | |
| 2005/0049550 A1 | 3/2005 | Kirchhofer et al. | |
| 2005/0154352 A1 | 7/2005 | Gurtner et al. | |
| 2005/0177114 A1 | 8/2005 | Michel et al. | |
| 2005/0261634 A1 | 11/2005 | Karlsson | |

(56) References Cited

U.S. PATENT DOCUMENTS

| | | | |
|---|---|---|---|
| 2006/0100590 A1* | 5/2006 | Thorne, Jr. | A61M 5/284 604/218 |
| 2006/0111666 A1 | 5/2006 | Hommann et al. | |
| 2006/0178638 A1 | 8/2006 | Reynolds | |
| 2006/0178644 A1 | 8/2006 | Reynolds | |
| 2006/0254788 A1 | 11/2006 | Bucher | |
| 2006/0258988 A1 | 11/2006 | Keitel et al. | |
| 2007/0027430 A1 | 2/2007 | Hommann | |
| 2007/0060875 A1 | 3/2007 | Bassarab et al. | |
| 2007/0060877 A1 | 3/2007 | Bassarab et al. | |
| 2007/0129673 A1 | 6/2007 | Bassarab et al. | |
| 2007/0163366 A1 | 7/2007 | Jeong et al. | |
| 2007/0197975 A1 | 8/2007 | Burren et al. | |
| 2007/0270739 A1 | 11/2007 | Kirchhofer et al. | |
| 2008/0045889 A1 | 2/2008 | Gerondale | |
| 2008/0071226 A1 | 3/2008 | Moser et al. | |
| 2008/0126102 A1 | 5/2008 | Shirakawa et al. | |
| 2008/0300550 A1 | 12/2008 | Schiller et al. | |
| 2008/0319400 A1* | 12/2008 | Thorne, Jr. | A61M 5/284 604/191 |
| 2009/0137964 A1 | 5/2009 | Enggaard et al. | |
| 2009/0157041 A1 | 6/2009 | Pettis et al. | |
| 2009/0209920 A1 | 8/2009 | Moller et al. | |
| 2009/0227960 A1* | 9/2009 | Milijasevic | A61M 5/16881 604/246 |
| 2009/0240195 A1 | 9/2009 | Schrul et al. | |
| 2009/0247985 A1 | 10/2009 | Melsheimer et al. | |
| 2009/0254027 A1 | 10/2009 | Moller | |
| 2010/0030551 A1 | 2/2010 | Ark et al. | |
| 2010/0036320 A1 | 2/2010 | Cox et al. | |
| 2010/0069845 A1 | 3/2010 | Marshall et al. | |
| 2010/0082013 A1* | 4/2010 | Braga | A61M 5/31596 604/518 |
| 2010/0087799 A1 | 4/2010 | Galbraith et al. | |
| 2010/0185156 A1 | 7/2010 | Kanner et al. | |
| 2010/0262074 A1 | 10/2010 | Seiferlein et al. | |
| 2010/0274198 A1 | 10/2010 | Bechtold | |
| 2010/0323322 A1 | 12/2010 | Jessop et al. | |
| 2010/0327007 A1 | 12/2010 | Fransson et al. | |
| 2011/0060274 A1 | 3/2011 | Kuhn | |
| 2011/0100921 A1 | 5/2011 | Heinrich | |
| 2011/0152784 A1 | 6/2011 | Veasey et al. | |
| 2011/0152822 A1 | 6/2011 | Drunk et al. | |
| 2011/0196310 A1 | 8/2011 | Cronenberg | |
| 2011/0201999 A1 | 8/2011 | Cronenberg et al. | |
| 2011/0224610 A1* | 9/2011 | Lum | A61M 5/38 604/125 |
| 2011/0224622 A1 | 9/2011 | Karlsson | |
| 2011/0230827 A1 | 9/2011 | Mori et al. | |
| 2012/0041366 A1 | 2/2012 | Fayyaz et al. | |
| 2012/0046613 A1 | 2/2012 | Plumptre | |
| 2012/0078171 A1 | 3/2012 | Seiferlein et al. | |
| 2012/0078195 A1 | 3/2012 | Harms et al. | |
| 2012/0089100 A1 | 4/2012 | Veasey et al. | |
| 2012/0095413 A1 | 4/2012 | Nzike et al. | |
| 2012/0118139 A1 | 5/2012 | Seiferlein et al. | |
| 2012/0130316 A1 | 5/2012 | Boyd et al. | |
| 2012/0136298 A1 | 5/2012 | Bendix et al. | |
| 2012/0136306 A1 | 5/2012 | Bartha | |
| 2012/0136315 A1 | 5/2012 | Wieselblad et al. | |
| 2012/0172816 A1 | 7/2012 | Boyd et al. | |
| 2012/0209171 A1 | 8/2012 | Vedrine et al. | |
| 2012/0283646 A1 | 11/2012 | Kouyouimjian et al. | |
| 2012/0289929 A1 | 11/2012 | Boyd et al. | |
| 2012/0310168 A1 | 12/2012 | Plumptre et al. | |
| 2013/0018327 A1 | 1/2013 | Dasbach et al. | |
| 2013/0046245 A1 | 2/2013 | Raad et al. | |
| 2013/0053789 A1 | 2/2013 | Harms et al. | |
| 2013/0096513 A1 | 4/2013 | Smith | |
| 2013/0131605 A1 | 5/2013 | Hiles | |
| 2013/0190719 A1 | 7/2013 | Smith et al. | |
| 2013/0211326 A1 | 8/2013 | Dasbach et al. | |
| 2013/0218098 A1 | 8/2013 | Chung | |
| 2013/0245562 A1 | 9/2013 | Kouyoumjian et al. | |
| 2013/0253433 A1 | 9/2013 | Senior et al. | |
| 2014/0025594 A1 | 1/2014 | Schmitz | |

FOREIGN PATENT DOCUMENTS

| | | |
|---|---|---|
| DE | 102004055298 | 5/2006 |
| EP | 0513128 | 11/1992 |
| EP | 0829268 | 3/1998 |
| EP | 1923085 | 5/2008 |
| EP | 1974761 | 10/2008 |
| EP | 2263721 | 12/2010 |
| EP | 2263722 | 12/2010 |
| EP | 2514454 | 10/2012 |
| FR | 2847887 | 6/2004 |
| JP | 7136264 | 5/1995 |
| KR | 1020110041826 | 4/2011 |
| WO | 9204926 | 4/1992 |
| WO | 2004037326 | 5/2004 |
| WO | 2006058435 | 6/2006 |
| WO | WO2006/079898 | 8/2006 |
| WO | WO2009/141005 | 11/2009 |
| WO | WO2010/003262 | 1/2010 |
| WO | WO2010/105376 | 9/2010 |
| WO | 2011131775 | 10/2011 |
| WO | WO2011/131779 | 10/2011 |
| WO | 2011154488 | 12/2011 |
| WO | WO2012/010832 | 1/2012 |
| WO | 2012072568 | 6/2012 |
| WO | 2012085017 | 6/2012 |
| WO | WO2012/128699 | 9/2012 |
| WO | WO2012/152666 | 11/2012 |
| WO | WO2013/033227 | 3/2013 |
| WO | WO2013/043861 | 3/2013 |
| WO | 2013112474 | 8/2013 |

OTHER PUBLICATIONS

International Search Report and Written Opinion dated May 15, 2013 for PCT/US2013/022561.
Office Action dated Sep. 12, 2013 for U.S. Appl. No. 13/385,627.
European Search Report dated Oct. 28, 2015 for EP13741261.5.

* cited by examiner

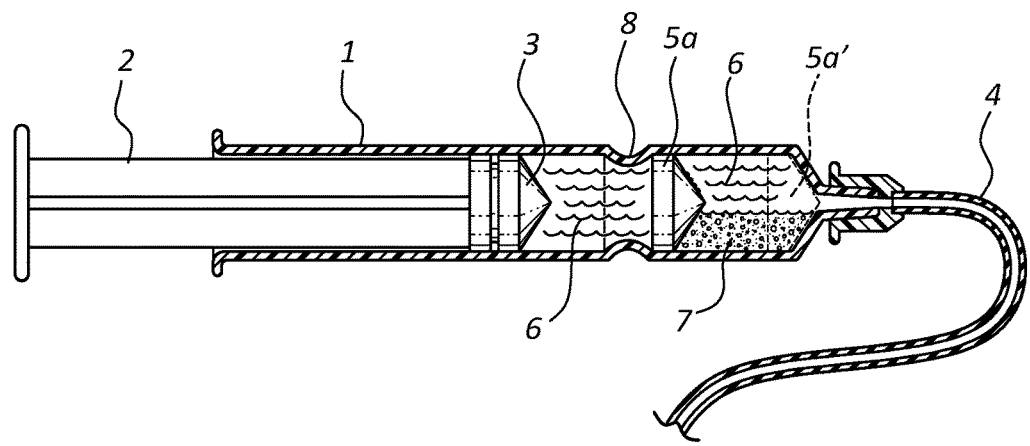
FIG. 1
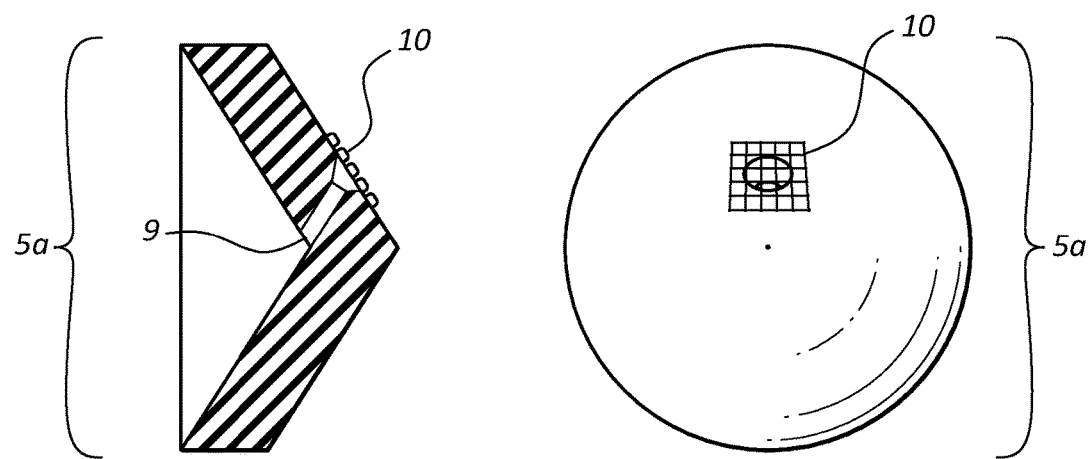
FIG. 2A  FIG. 2B

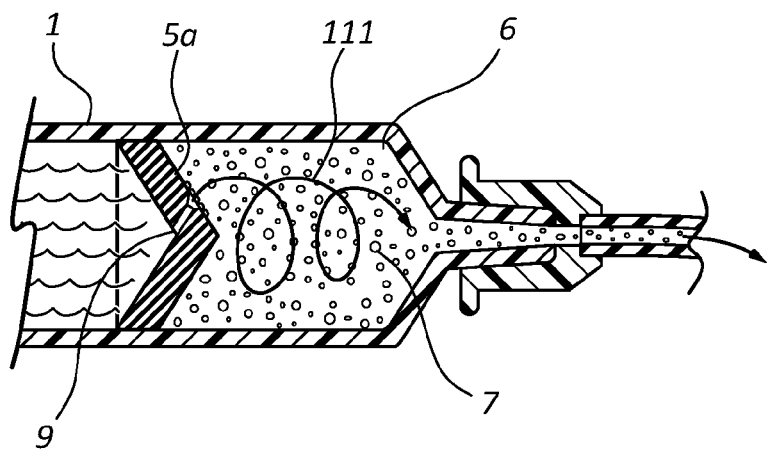
FIG. 3
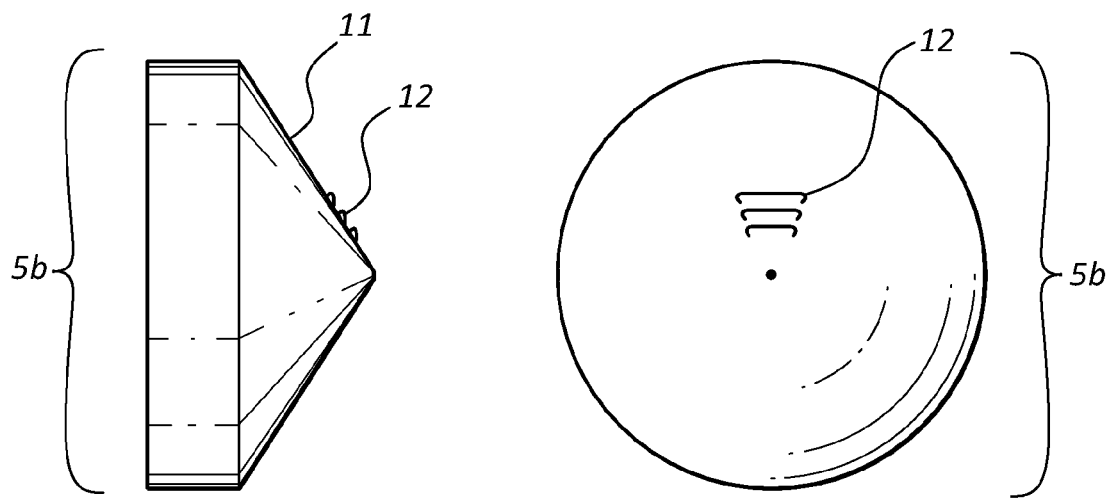
FIG. 4A
FIG. 4B
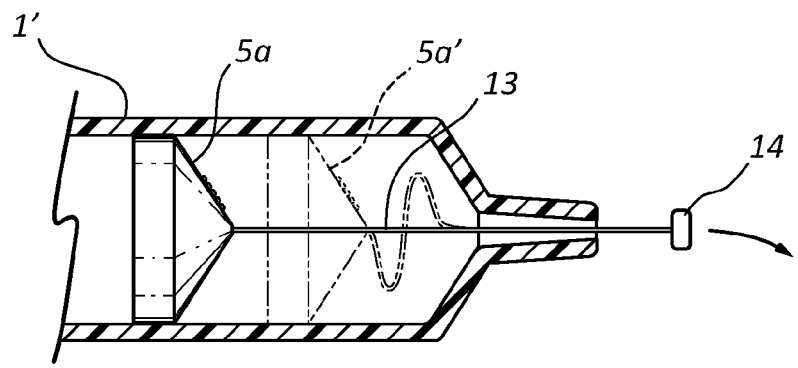
FIG. 5

MIXING SYRINGE

RELATED APPLICATIONS

This is a continuation-in-part of International Patent Application No. PCT/US2013/022561, with an international filing date of Jan. 22, 2013, which claims priority to both U.S. patent application Ser. No. 13/385,627, titled Mixing Syringe, filed on Feb. 28, 2012, and to U.S. patent application Ser. No. 61/632,263 filed on Jan. 23, 2012. All of these applications are hereby incorporated by reference in their entireties.

TECHNICAL FIELD

The present disclosure relates to the medical field, particularly to percutaneous procedures such as embolization.

BACKGROUND OF THE INVENTION

In certain medical procedures, such as blood vessel embolization, it may be desired to inject particles into the body. Such a procedure may be a minimally invasive alternative to surgery. One purpose of embolization is to prevent blood flow to an area of the body, which may effectively shrink a tumor, such as a uterine fibroid (leiomyoma). Further, such procedures may also shrink other kinds of tumors or block blood flow to or within an aneurysm or arteriovenous malformation. Embolization may be done by injecting blocking particles into a blood vessel.

Such procedures may be carried out as an endovascular procedure, such as by a radiologist in an interventional suite. Some patients may have the treatment carried out with little or no sedation, although this may depend on the organ to be embolized.

Access to the organ in question may be acquired by means of a guidewire and catheter. The position of the correct artery or vein supplying the undesired tissue in question may be located by X-Ray images. These images may then be used as a map for the radiologist to gain access to the correct vessel by selecting an appropriate catheter and/or wire, depending on the shape of the surrounding anatomy.

The blocking particles may be mixed into a saline solution; additionally, in some instances, a contrast agent may be added (for example, to make the mixture opaque to X-rays). The blocking particles may be of certain sizes, such as between 0.1 mm and 1 mm, and may be configured to block a blood vessel at a particular diameter. Such particles may tend to settle quickly out of the mixture, as the particles may be denser than the liquid carrying them, or they may float as the particles may be less dense than the liquid carrying them. Settling or floating may result in an uneven concentration of particles during the injection. In some instances, the settling or floating may occur in as little as a few seconds. It may be difficult or problematic to continually shake the syringe used for injection, however, as the entire procedure may be performed in a few seconds and the doctor has to concentrate on injecting the correct amount. Thus, it is desired to have a syringe configured to keep the particles uniformly dispersed in the carrying solution regardless of delays in the injection process or speed of the injection. Additionally, since the syringes used may be low-cost disposable items, in some embodiments, the device used to keep the particles uniformly dispersed may also be very low-cost and/or disposable. Some embodiments of mixing syringes within the scope of this disclosure may comprise the following attributes:

A. Ability to be re-filled multiple times during a procedure. Thus, in certain embodiments, the mixing syringe may not comprise certain single-use designs, which include rupturing of a membrane to allow mixing.

B. Generate a strong mixing action, for example, by creating a vortex or a jet-like liquid flow pattern in the mixture.

C. Use the minimum modification to a standard syringe.

Certain mixing syringes, such as disclosed in U.S. Pat. No. 7,883,490, are designed to mix together two materials stored separately in two compartments. They are not designed to stir up a pre-mixed solution. Additionally, certain syringes which may be designed to stir up embolization mixtures, such as disclosed in U.S. Patent Application Publication No. 2009/0247985, are needlessly and highly complex. Also, existing mixing syringes are not designed to be filled with the pre-mixed solution just before use. This filling step may be part of embolization procedures, however, as the correct volume and ratio of saline, particles and contrast agent may be customized to the procedure by the doctor. A mixing syringe according to the present disclosure, may allow filling and injecting at any time, while keeping the solution stirred up during injection. Further, in some embodiments, a mixing syringe according to the present disclosure may be re-used several times during a procedure, if a practitioner desires to inject more particles. In some embodiments, a mixing syringe according to the present disclosure may be manufactured out of a standard syringe, which may be a low-cost item.

SUMMARY OF THE DISCLOSURE

In some embodiments, a movable mixing disc is inserted into a standard syringe to create a mixing assembly. A mixing disc according to the present disclosure may comprise a small hole which may be covered by a fine screen, coupled to, or in communication with, a porous matrix, and/or covered by louvered openings. Such designs may be configured to allow only saline or other liquids to get behind the mixing disc. In some embodiments, when a plunger of the mixing syringe is pressed, saline or other solution disposed therein emerges from the mixing disc hole as a high velocity jet, stirring up settled particles. In some embodiments, the mixing disc may be moved forward by virtue of a pressure difference created by a pressure drop across the mixing disc, such as a pressure drop created as the plunger is displaced to induce fluid flow across the mixing disc. Additionally, in some embodiments, the mixing disc may be pushed forward by the plunger, as the ejection continues, in order to eliminate any unused volume.

BRIEF DESCRIPTION OF THE DRAWINGS

FIG. 1 is a side cross-sectional view of a first embodiment of a mixing syringe, including a mixing disc.

FIG. 2A is a cross-sectional view of the mixing disc of FIG. 1.

FIG. 2B is a front view of the mixing disc of FIG. 2A.

FIG. 3 is an enlarged side cross-sectional view of a portion of the mixing syringe of FIG. 1, showing the action of the mixing disc.

FIG. 4A is a cross-sectional view of another embodiment of a mixing disc, stamped out of sheet metal.

FIG. 4B is a front view of the mixing disc of FIG. 4A.

FIG. 5 is a side cross-sectional view of another embodiment of a portion of a mixing syringe.

DETAILED DESCRIPTION

Figure 6:
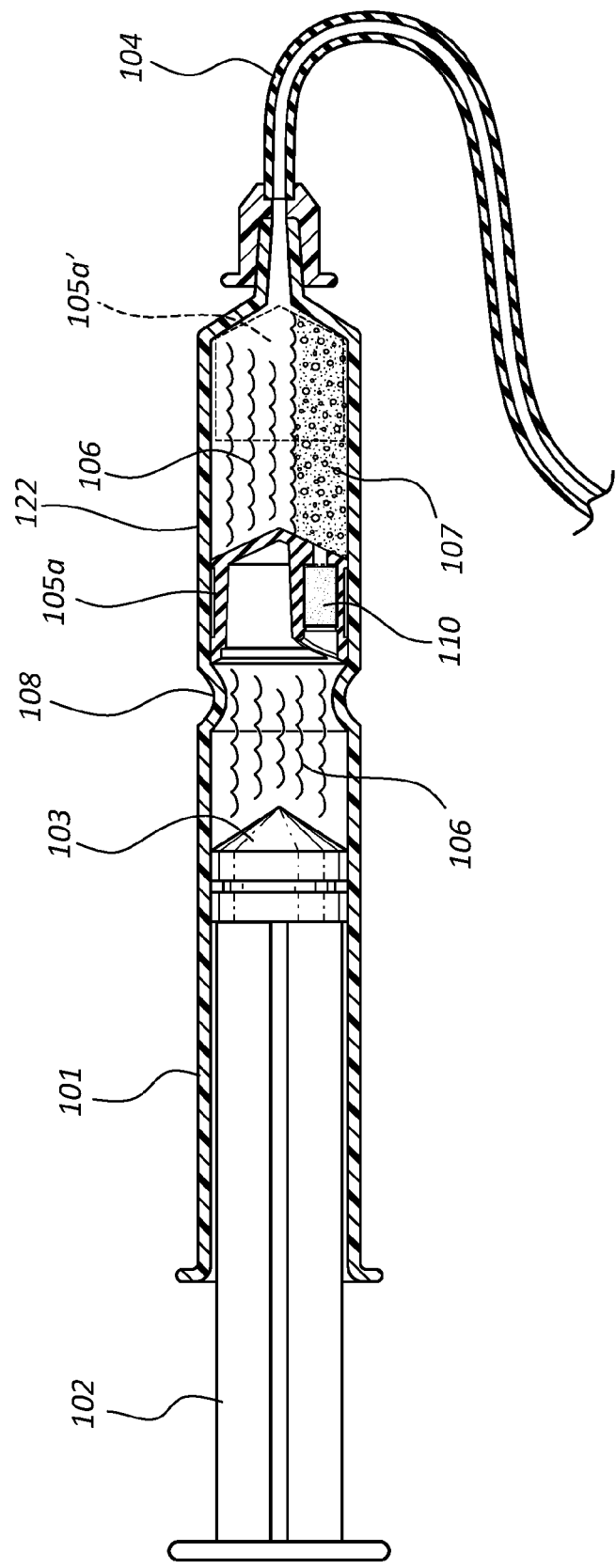
FIG. 6 is a side cross-sectional view of another embodiment of a mixing syringe.

FIG. 1 is a side cross-sectional view of a first embodiment of a mixing syringe which includes a mixing disc 5a. The mixing syringe of FIG. 1, may comprise a standard syringe with the addition of a mixing disc 5a. In the illustrated embodiment, the syringe 1 includes a plunger 2 and a seal 3 configured to eject a liquid 6 from the syringe 1 via a tube 4. In the illustrated embodiment, the mixing syringe further comprises a mixing disc 5a. In some embodiments the mixing disc 5a may function similarly to a piston disposed within a cylinder. An initial position of mixing disc 5a is shown in broken lines and labeled 5a'. Further, when the mixing disc 5a is disposed in the initial position shown as 5a', the plunger seal 3 may be disposed distally such that it contacts the mixing disc 5a in the 5a' position. The plunger 2 may then be drawn back proximally, creating a vacuum, to draw liquid 6 and particles 7 into the syringe 1 through the tube 4. Thus, the seal 3 may move away from mixing disc 5a, creating a gap between the seal 3 and the mixing disc 5a. The mixing disc 5a may also move, for example it may move proximally until stopped by a slight ridge 8 disposed on the syringe 1. This movement may be at least partially induced by a pressure drop across the mixing disc 5a as the plunger 2 is drawn back. Stated differently, as the plunger 2 is drawn back, fluid disposed distal of the mixing disc 5a may exert a greater force on mixing disc 5a than fluid on the proximal side of the mixing disc 5a. Such a fluid force may cause the mixing disc 5a to move in a proximal direction. In the illustrated embodiment, the size of the ridge 8 is exaggerated for clarity. In some embodiments, the ridge 8 may reduce the inside diameter of the syringe 1 by about 0.2 mm to about 0.3 mm. The flexible seal 3 may be configured to easily pass over the ridge 8. Particles 7 sucked into the syringe 1 via the tube 4, may tend to quickly settle, as shown in FIG. 1. The particles 7 may not accumulate in the section between the plunger seal 3 and the mixing disc 5a, as mixing disc 5a may include a filter element with pore sizes smaller than the particles 7.

The mixing disc 5a may also be displaced distally during use. For example, distal displacement of the plunger 2 may create a pressure drop across the mixing disc 5a. This pressure drop may induce flow through openings in the mixing disc 5a as well as induce movement of the mixing disc 5a. In some embodiments, the mixing syringe may be configured such that the mixing disc 5a is proximally displaced at a different rate than the plunger 2. In some instances the rates of displacement may be configured such that the seal 3 contacts the mixing disc 5a when the volume of fluid on either side of the mixing disc 5a is zero. For example, if the syringe contained equal volumes of fluid on the proximal and distal sides of the mixing disc 5a, distal displacement of the mixing disc 5a at one-half the velocity of the plunger 2, may be configured to displace all the fluid from the mixing syringe just as the seal 3 contacts the mixing disc 5a. Further, configurations wherein proximal displacement of the mixing disc 5a (and proximal fluid flow across the mixing disc 5a) is related to pressure differences induced by displacement of the plunger 2 and/or seal 3 are also within the scope of this disclosure. Rates of proximal displacement may likewise be related.

FIGS. 2A and 2B illustrate one embodiment of a filter element. In some embodiments, the filter element may comprise a screen or a plurality of louvers. Referring to mixing disc 5a, shown in FIG. 1-2B, the mixing disc 5a may comprise one or more holes 9 which may be covered by filter mesh, screen 10. In the illustrated embodiment, the hole 9 is chamfered under the screen 10 to increase the effective area of the screen. The screen 10 can also be mounted as a flexible flap, and may be configured to be pushed out of the way during ejection of the fluid 6. The conical shapes on the proximal and distal sides of disc 5a may be matched to the shape of the conical seal 3, and the conical tip of the syringe 1, respectively. This may eliminate trapped fluid between the seal 3 and the syringe outlet at the end of the stroke, as fluid 6 is ejected. The conical shape of the proximal side of disc 5a may also aid the removal of any trapped air bubbles, as the bubbles may float to the top of disc 5a and escape when the syringe 1 is held vertically. During use, movement of the plunger 3 towards disc 5a may force the liquid 6 through the hole 9 at a high velocity, tending to mix up particles 7 and liquid 6 disposed on the distal side of the mixing disc 5a. For example, FIG. 3 illustrates the mixing of these components as fluid 6 passes through the mixing disc 5a.

Referring to FIGS. 1-3, the plunger 2 may be displaced until the seal 3 touches the mixing disc 5a which is also in contact with the ridge 8. The mixing disc 5a may then be pushed forward towards the tube 4 until the syringe 1 is empty and the mixing disc 5a is in position 5a'. The operation may also be repeated, if desired.

In some embodiments, the hole 9 may be disposed at an angle to the axis of the syringe 1, which may create a vortex 111 as fluid passes through the hole 9. Further, in some embodiments, the vortex 111 may be created by forming the hole 9 as a curved arc, both in the plane of the drawing and also in the plane perpendicular to the drawing.

In some embodiments, the mixing disc 5a may be molded in one piece, which may include the screen 10. Alternatively, in other embodiments, the screen 10 can be bonded to molded disc 5a. In some embodiments, the fit between the mixing disc 5a and the bore of the syringe 1 may only be configured to prevent particles 7 from passing the mixing disc 5a. Thus, in embodiments wherein the particles 7 are relatively large, the fit between these components may allow for variation. In some embodiments, the diameter of the mixing disc 5a may be between about 0.1 mm and about 0.2 mm smaller than the inside diameter of the syringe 1.

While the example given above focuses on embolization, the present disclosure is relevant to any application comprising mixing any two components, including two liquids.

Additionally, in some embodiments, such as shown in FIGS. 4A and 4B, a mixing disc 5b can be made out of pressed sheet metal 11. In some such embodiments, the hole and screen (9 and 10, respectively, of FIGS. 2A and 2B) may be replaced by miniature stamped louvers 12 (similar to a miniature venetian blind) acting both as a screen and as a flow director. In some instances 316L stainless steel or aluminum, with thickness from about 0.1 mm to 0.3 mm may be used to form the mixing disc 5b. The thin wall of the mixing disc 5b may be configured to allow a seal (such as seal 3 of FIG. 1) to enter into the hollow disc and squeeze out all the liquid during use.

In some embodiments, the slight ridge 8 may be formed in standard syringes by briefly heating up the area of ridge 8 and pressing the walls in slightly, using a split ring slightly smaller than the outside diameter of the syringe. Thus, the present disclosure is relevant for use in connection with standard syringes, not custom molded syringes. Further, other ways of creating a ridge 8 without custom molding include pressing a thin walled ring into the syringe, such that the ring is held in place by friction.

FIG. 5 is a side cross-sectional view of another embodiment of a portion of a mixing syringe 1'. As shown in FIG. 5, in some embodiments, a syringe within the scope of this disclosure may be manufactured out of a standard disposable syringe 1', without any direct modifications to the syringe 1'. In the embodiment of FIG. 5, the mixing disc 5a from FIGS. 2A and 2B is attached to the outlet side of the syringe 1' with a short string 13 that only allows the mixing disc 5a to move a limited distance. The string 13 may be bonded by heat to the syringe 1' or, as shown in the illustrated embodiment, may use an anchor 14.

FIG. 6 is a side cross-sectional view of another embodiment of a mixing syringe. The embodiment of FIG. 6 may include components that resemble components of FIG. 1 in some respects. For example, the embodiment of FIG. 6 includes a syringe 101 that may resemble the syringe 1 of FIG. 1. It will be appreciated that all the illustrated embodiments have analogous features. Accordingly, like features are designated with like reference numerals, with leading digits added to increment each reference numeral by 100. (For instance, the syringe is designated "1" in FIG. 1 and an analogous syringe is designated as "101" in FIG. 6.) Relevant disclosure set forth above regarding similarly identified features thus may not be repeated hereafter. Moreover, specific features of the mixing syringe and related components shown in FIG. 6 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the mixing syringe and related components of FIG. 6. Any suitable combination of the features, and variations of the same, described with respect to the mixing syringe and components illustrated in FIG. 1, can be employed with the mixing syringe and components of FIG. 6, and vice versa. This pattern of disclosure applies equally to further embodiments depicted in subsequent figures and described hereafter.

In the embodiment of FIG. 6, the syringe 101 may comprise a cylindrical body 122 which may be configured to contain a first substance and a second substance, for example a liquid 106 and a plurality of particles 107. Further, the syringe 101 may include a plunger 102 and a seal 103 configured to eject a liquid 106 from the syringe 101 via a tube 104. The mixing syringe further comprises a mixing disc 105a. In the illustrated embodiment, an initial position of the mixing disc 105a is shown in broken lines as 105a'. Further, when the mixing disc 105a is disposed in the initial position shown as 105a', the plunger seal 103 may be disposed distally such that it contacts the mixing disc 105a in the 105a' position. The plunger 102 may then be drawn back proximally, creating a vacuum, to draw liquid 106 and particles 107 into the syringe 101 through the tube 104. Thus, the seal 103 may move away from mixing disc 105a, creating a gap between the seal 103 and the mixing disc 105a. The mixing disc 105a may also move, for example it may move proximally until stopped by a slight ridge 108 disposed on the syringe 101. In the illustrated embodiment, the size of the ridge 108 is exaggerated for clarity. In some embodiments, the ridge 108 may reduce the inside diameter of the syringe 101 by about 0.2 mm to about 0.3 mm. The flexible seal 103 may be configured to easily pass over the ridge 108. Particles 107 disposed within the syringe 101 may tend to settle or accumulate within the syringe 101, as illustrated in FIG. 6. In some embodiments, the mixing disc 105a may be configured to prevent the migration of particles 107 proximally beyond the mixing disc 105. For example, the mixing disc 105a may comprise a filter element, such as a porous member 110, with pore sizes configured to allow liquid 106 to cross the porous member 110 while restricting the passage of particles 107.

In the illustrated embodiment, the conical shape of the distal end of mixing disc 105a is substantially matched to the shape of the conical tip of the syringe 101. This may eliminate trapped fluid between the mixing disc 105a and the syringe outlet upon actuation of the plunger 102. When seal 103 contacts mixing disc 105a the mixing disc 105a may be pushed forward towards the tube 104 until the syringe 101 is substantially empty and disc 105a is in position 105a'.

Figure 7:
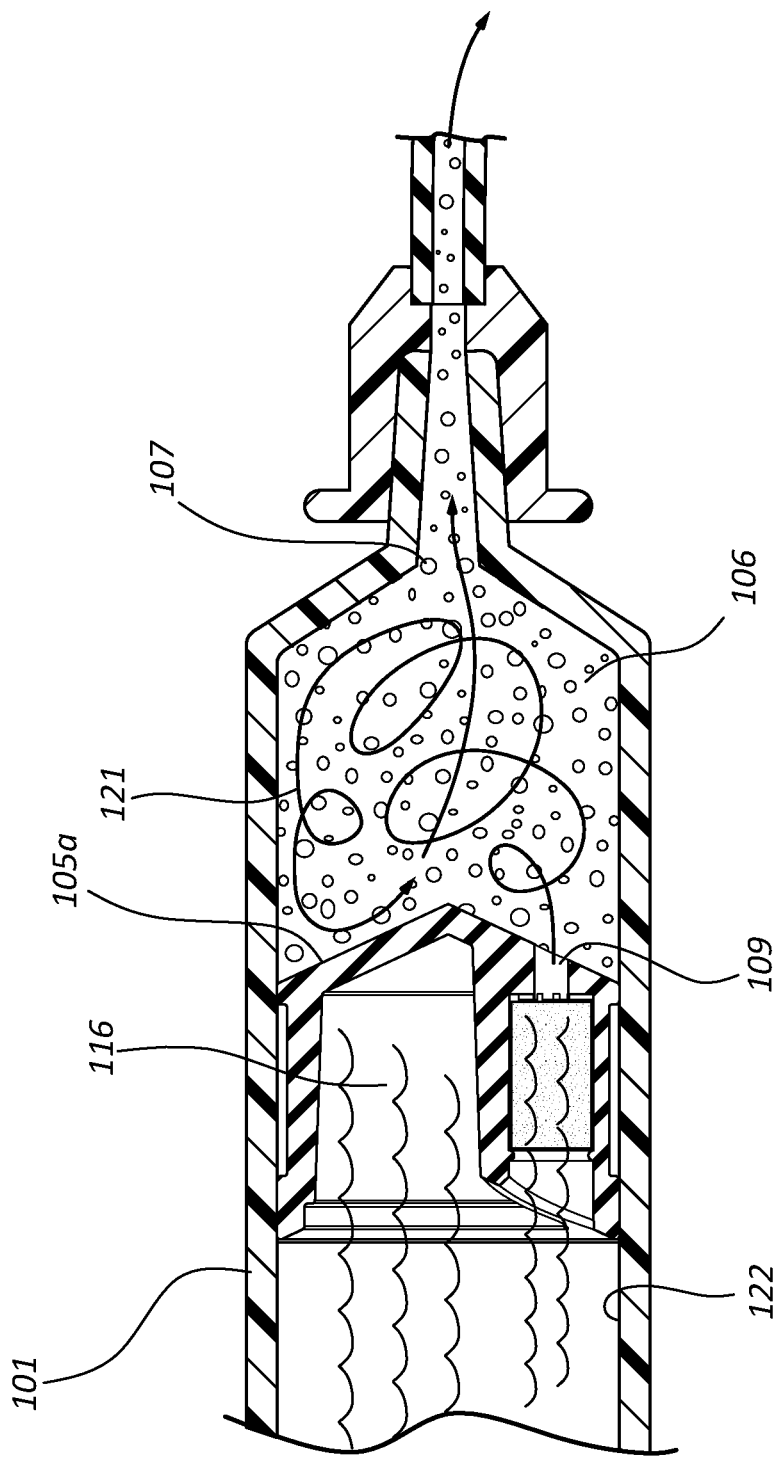
FIG. 7 is an enlarged side cross-sectional view of a portion of the mixing syringe of FIG. 6, showing the action of the mixing disc.

FIG. 7 is an enlarged side cross-sectional view of a portion of the mixing syringe of FIG. 6, showing possible action of the mixing syringe. In the illustrated embodiment, as plunger 102 is moved towards disc 105a the liquid 106 may be ejected via a hole 109, mixing up the particles 107 and the liquid 106. The relative size of the hole 109 as well as the rate at which the plunger 102 is displaced may be configured to impart sufficient velocity to the liquid 106 pushed through the hole 109 to mix the particles 107 and liquid 106. As liquid 106 is forced through the hole 109 it may collide with and disrupt the settled particles 107. Additionally the liquid 106 may collide with an end of the cylindrical body 122 and create a tumbling motion in the mixture which may mix the first particles 107 and liquid 106. A potential flow pattern 121 is indicated by the arrows in FIG. 7. The entire operation can also be repeated, if desired. In some embodiments, the mixing syringe may also or alternatively be used to mix a first substance and a second substance, including instances wherein both substances are liquids, at least one substance is a powder, and so forth. Further, the mixing syringe may be used to mix a plurality of substances. In one embodiment the first substance may comprise a plurality of particles and/or a powder while the second substance may comprise a liquid. In another embodiment the first substance may comprise a liquid and the second substance may comprise a plurality of particles and/or a powder. Mixing powders, particles, liquid, or other elements with a gas or any other fluid are also within the scope of this disclosure.

In the illustrated embodiment, the hole 109 is positioned off center from a central axis of the mixing disc 105a. This positioning of hole 109 may be configured to create or increase the dispersive flow pattern 121 in the mixture. For example, an off center hole 109 may introduce liquid 106 such that it initially contacts settled particles 107 within the syringe 101. An off center hole 109 may further be configured to create a tumbling type flow within the syringe 101. Again, the dispersive flow pattern 121 may result in mixing any number of substances that may be disposed in the syringe 101.

The mixing disc 105a of FIG. 7 further comprises a hollow chamber 116. As further described below, mixing discs with no hollow chamber 116 are also within the scope of this disclosure. Absence of a hollow chamber 116 may be configured to aid in de-bubbling the fluid disposed proximal of the mixing disc 105a, and may be shaped to direct any bubbles to the hole 109 when the syringe 101 is held vertically. Absence of a hollow chamber 116 may further decrease the amount of fluid needed to fill the syringe 101 and may avoid instances wherein unused fluid becomes trapped within the syringe 101.

Figure 8:
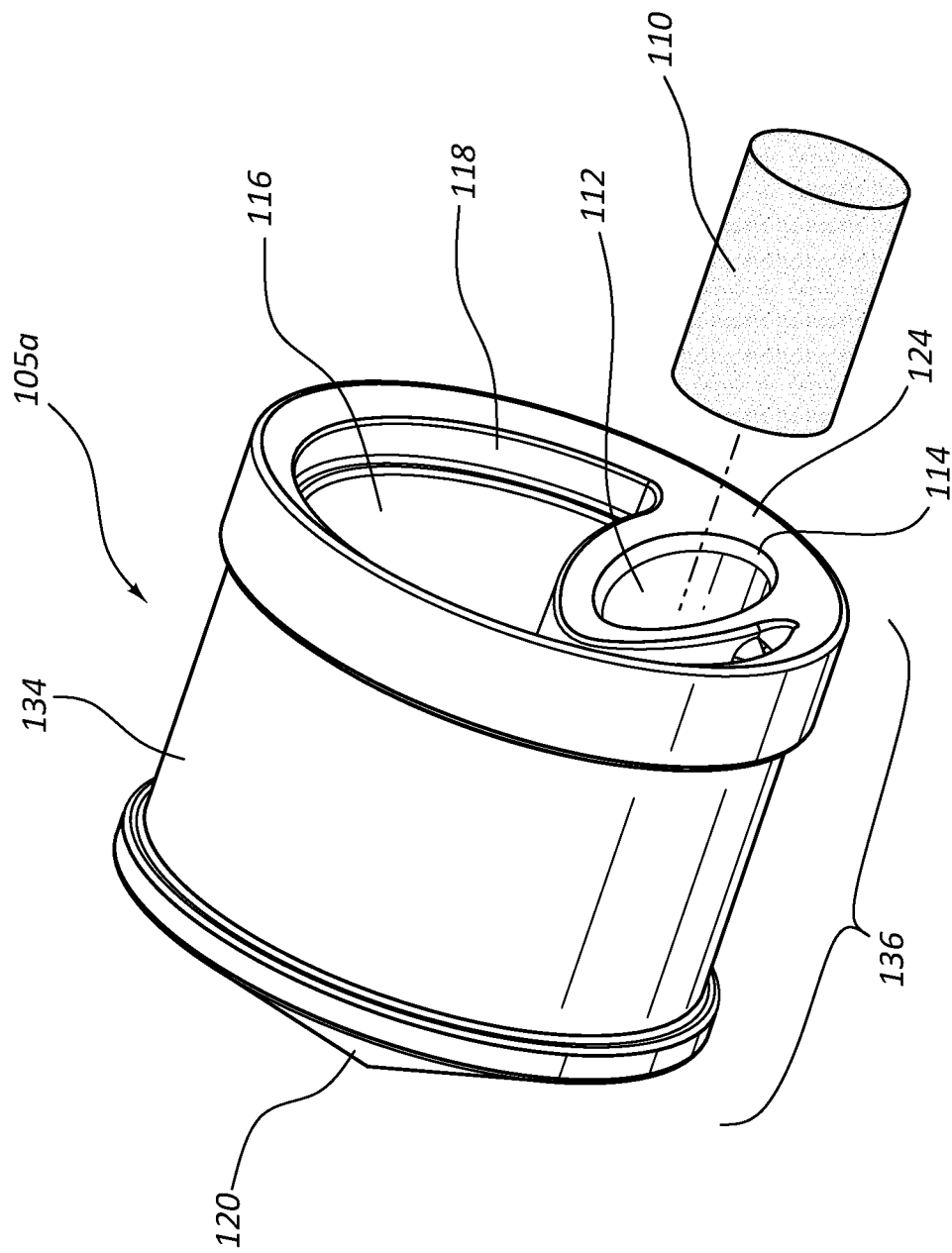
FIG. 8 is a perspective view of the mixing disc of the mixing syringe of FIG. 6, illustrating a porous member.

FIG. 8 is a perspective view of the mixing disc 105a of the mixing syringe of FIG. 6, further illustrating one embodiment of the porous member 110. In the illustrated embodiment, the mixing disc 105a comprises an elongate body 136 having a proximal end 124, a middle portion 134 and a distal end 120. Further, in the illustrated embodiment, a proximal opening 114 of a cavity 112 and a proximal opening 118 of the hollow chamber 116 are shown. The cavity 112 may be in fluid communication with the hole 109, the cavity 112 and hole 109 together creating a fluid passage across the mixing disc 105a. A porous member 110 may be disposed in the cavity 112. The porous member 110 may comprise a polymeric material or an elastomeric material, for example, Porex. The porous member 110 may be either hydrophilic or hydrophobic. Additionally, the porous member 110 may be manufactured by molding or extrusion, or any other method of manufacture.

The mixing disc 105a may thus be configured such that liquid forced through the mixing disc 105a passes through the porous member 110. The porous member 110 may be configured to prevent particles on one side of the mixing disc 105a from crossing the mixing disc 105a, while allowing fluid to cross the mixing disc 105a. Thus, the porous member 110 may be configured with pore sizes or an effective porosity configured to filter liquid within the syringe. In use, the porous member 110 may prevent particles disposed distally of the mixing disc 105a from being drawn through the mixing disc 105a as the plunger (102 of FIG. 6) is drawn back proximally to pull liquid into the syringe (101 of FIG. 6).

Figure 9B:
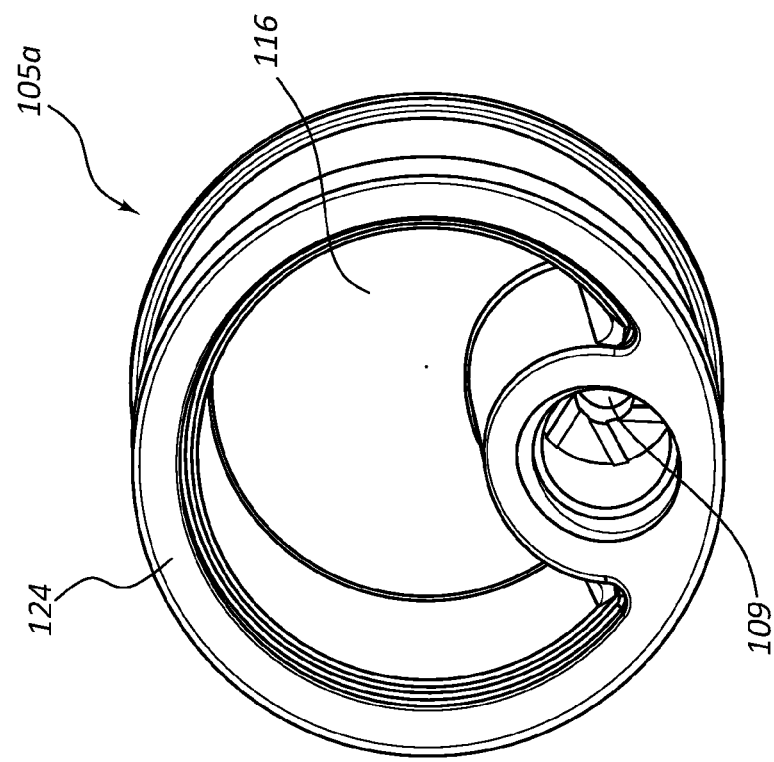
FIG. 9B is a perspective view of the mixing disc of FIG. 8 showing the proximal end thereof.
Figure 9A:
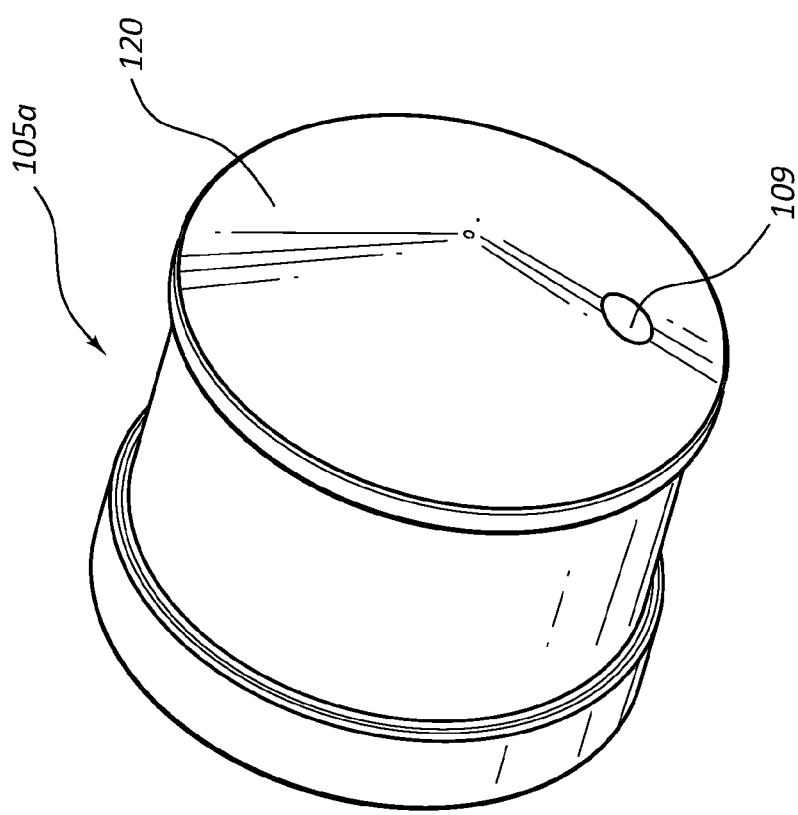
FIG. 9A is a perspective view of the mixing disc of FIG. 8 showing the distal end thereof.

FIG. 9A is a perspective view of the mixing disc 105a of FIG. 8 showing the distal end 120 thereof. FIG. 9B is a perspective view of the mixing disc 105a showing the proximal end 124 thereof. The off center positioning of the hole 109 from a central axis of the mixing disc 105a is shown in these Figures. In the illustrated embodiment, the mixing disc 105a further comprises a hollow chamber 116. The hollow chamber 116 may allow the mixing disc 105a to be made more economically by reducing the material of the mixing disc 105a and may allow for the mixing disc 105a to have a lighter final weight. Manufacture of a mixing disc 105a comprising a hollow chamber 116, as illustrated, may require less starting material and thus may decrease expenses involved in manufacture of an embodiment of the mixing disc 105a. As discussed above, in other embodiments, a mixing disc may be without a hollow chamber 116.

Figure 10B:
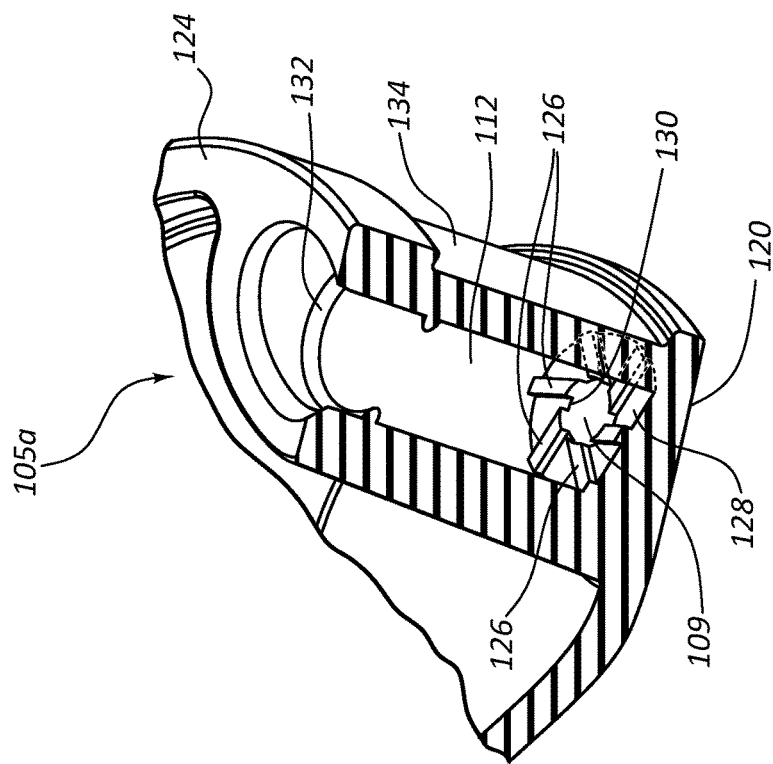
FIG. 10B is an enlarged cross-sectional partial perspective view showing the distal end of the mixing disc of FIG. 8.
Figure 10A:
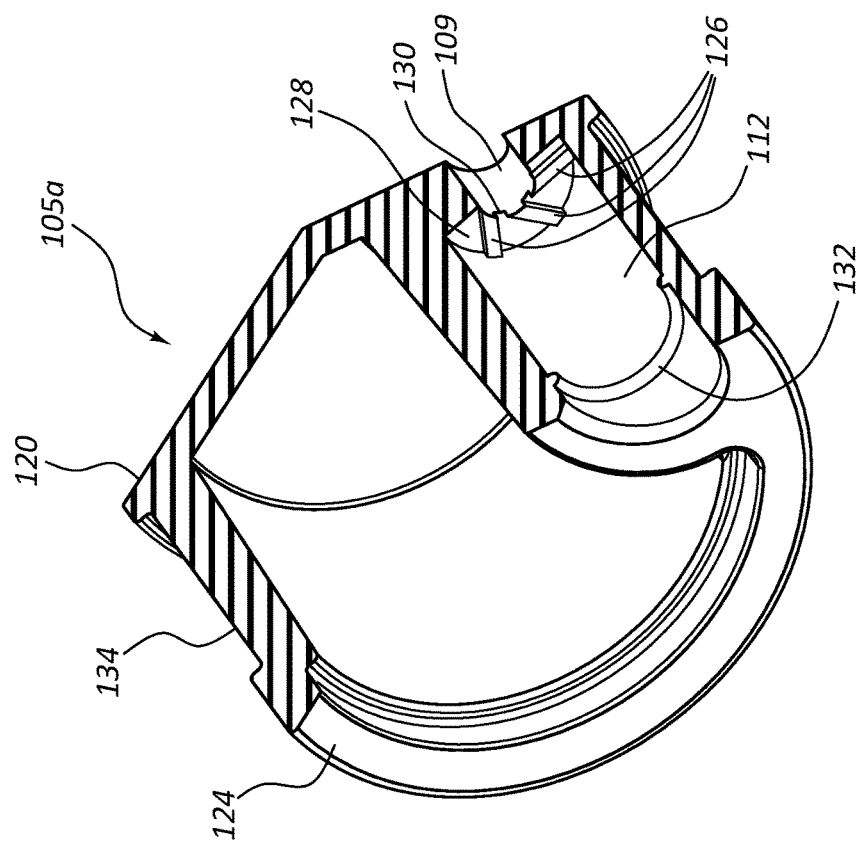
FIG. 10A is a cross-sectional perspective view showing the proximal end of the mixing disc of FIG. 8.

FIG. 10A is a cross-sectional perspective view showing the proximal end 124 of the mixing disc 105a. FIG. 10B is an enlarged cross-sectional partial perspective view showing the distal end 120 of the mixing disc 105a. Again, in the illustrated embodiment, mixing disc 105a has a cavity 112 in fluid communication with the hole 109 in the disc 105a. The cavity 112 and hole 109 may create a fluid passageway across the mixing disc 105a. Further, in some embodiments, the cavity 112 may comprise a plurality of baffles 126 disposed at or adjacent a distal end 128 of the cavity 112. In the illustrated embodiment, the diameter of the distal end 128 of the cavity 112 is greater than the diameter of a proximal opening 130 of the hole 109. In this embodiment, the baffles 126 extend radially from the proximal opening 130 of the hole 109 at the distal end 128 of the cavity 112. Further, in the illustrated embodiment, the baffles 126 extend at an angle less than ninety degrees in relation to a tangent line at the proximal opening 130 of the hole 109. In other embodiments, the baffles 126 may extend at any other angle, including larger and smaller angles. The baffles 126 may radially accelerate fluid forced through the cavity 112 (through the porous member 110 of FIG. 6), creating a dispersive effect on fluid forced through the hole 109. This dispersive effect may induce a flow pattern configured to further mixing liquids, particles, or other substances disposed within the syringe (101 of FIG. 6).

The cavity 112 may further comprise a retention ridge 132 disposed on an inside diameter of the cavity 112. The retention ridge 132 may be configured to couple the mixing disc 105a and the porous member (110 of FIG. 8). Referring both to FIG. 8 and FIGS. 10A and 10B, the retention ridge 132 may be configured to create an interference or snap fit with the porous member 110 as the porous member 110 is inserted into the cavity 112. In some embodiments, the porous member 110 may be removably coupled with the mixing disc 105a, while in another embodiment the porous member 110 may be permanently coupled with the mixing disc 105a. An adhesive or other coupling component may be used in addition to, or instead of, the retention ridge 132. In the illustrated embodiment, the retention ridge 132 is rounded; such a configuration may be configured to facilitate placement and displacement of the porous member 110 in the cavity 112. In other embodiments, the retention ridge 132 may be square, triangular, or otherwise shaped.

In the illustrated embodiment, the diameter of the proximal end 124 of the mixing disc 105a and the diameter of the distal end 120 of the mixing disc 105a are substantially equal, while the diameter of the middle portion 134 of the mixing disc 105a is less than the diameters of the distal 120 and proximal 124 ends of the mixing disc 105a. This configuration may decrease the contact between the disc 105a and an internal diameter of the syringe 101 while still maintaining a seal between the disc 105a and the internal diameter of the syringe 101. This configuration may also decrease the amount of friction between the outside diameter of the mixing disc 105a and the internal diameter of the syringe 101 as the plunger 102 is actuated by a user, and thus may facilitate actuation of the plunger 102 and seal 103. Embodiments wherein the middle portion 134 has substantially the same diameter as the distal 120 and proximal 124 ends, as well as embodiments wherein only one of these components extends all the way to the syringe body are likewise within the scope of this disclosure.

Figure 11B:
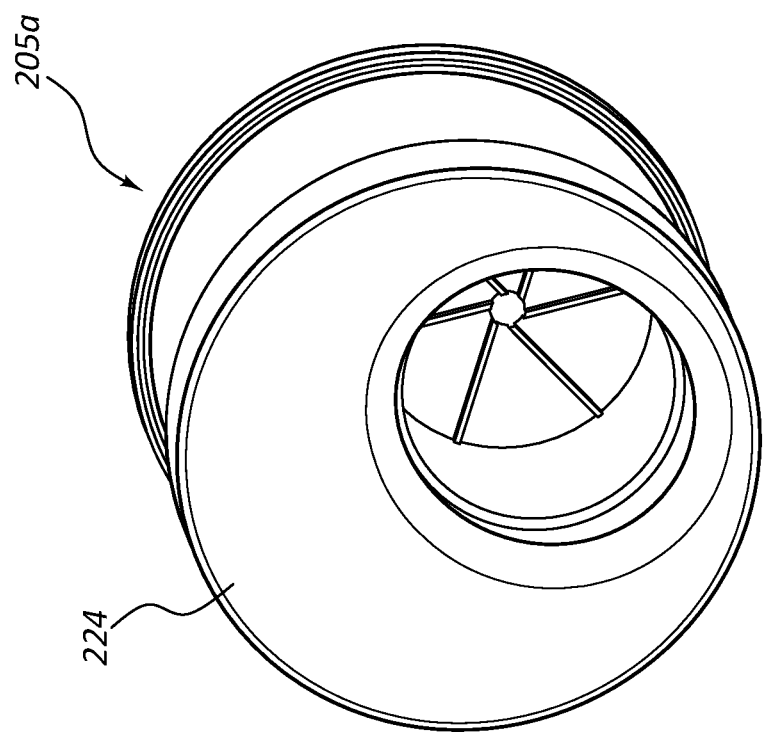
FIG. 11B is a perspective view showing the proximal end of the mixing disc of FIG. 11A.
Figure 11A:
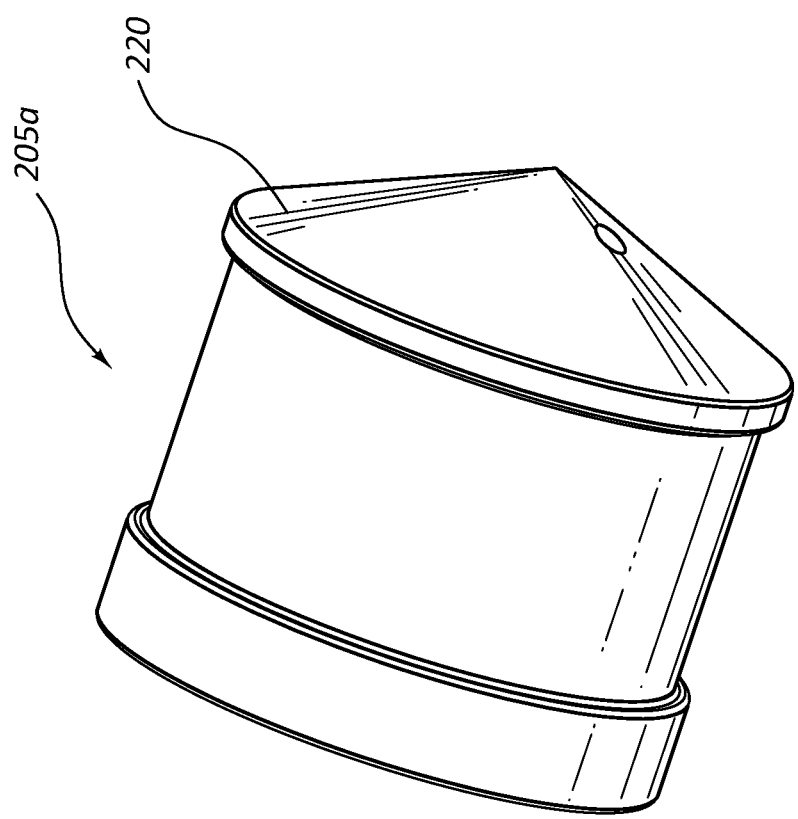
FIG. 11A is a perspective view showing the distal end of another embodiment of a mixing disc.

FIG. 11A is a perspective view showing a distal end 220 of another embodiment of a mixing disc 205a. FIG. 11B is a perspective view showing a proximal end 224 of the mixing disc 205a. In the embodiment of FIGS. 11A and 11B, as compared to the embodiment of FIGS. 10A and 10B, the mixing disc 205a does not comprise a hollow chamber (116 of FIG. 8). Again, such a configuration may decrease the amount of liquid that is potentially trapped between a seal (such as 103 of FIG. 6) and the mixing disc 205a upon ejection of a fluid or other material within a syringe. Additionally, such a configuration may aid in de-bubbling the syringe 101, as further discussed in connection with FIGS. 12A and 12B, below.

Figure 12B:
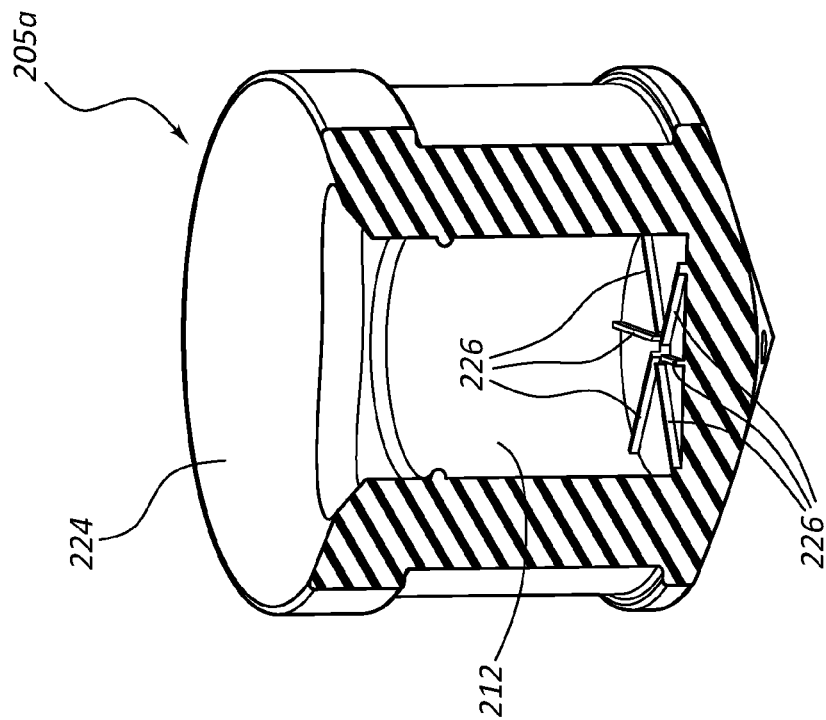
FIG. 12B is another cross-sectional perspective view of the mixing disc of FIG. 11A.
Figure 12A:
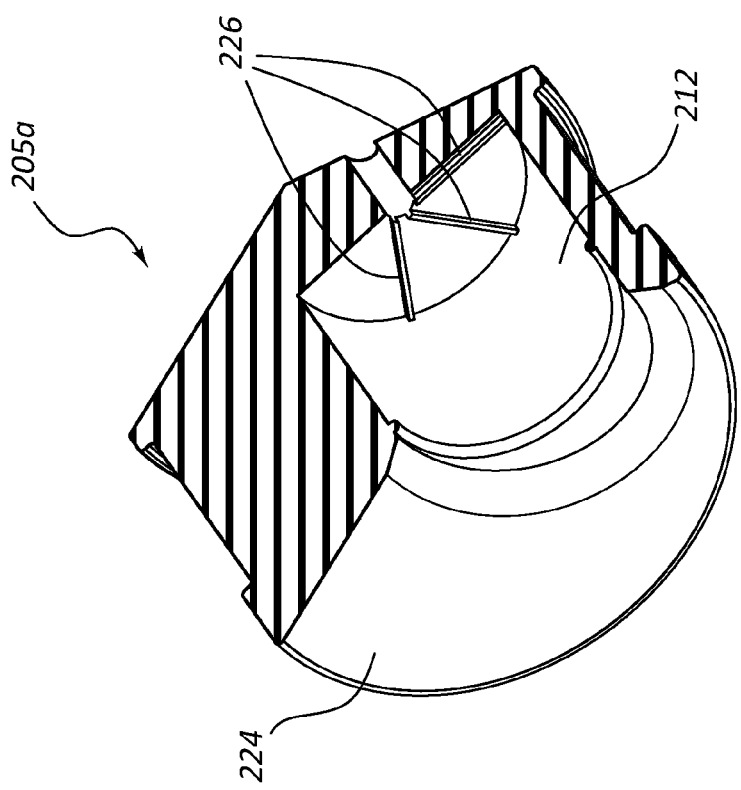
FIG. 12A is a cross-sectional perspective view showing the proximal end of the mixing disc of FIG. 11A.

FIG. 12A is a cross-sectional perspective view showing the proximal end 224 of the mixing disc 205a of FIG. 11A, and FIG. 12B is another cross-sectional perspective view of the mixing disc 205a. The mixing disc 205a of FIGS. 12A and 12B further comprises baffles 226 disposed within a fluid flow path through the mixing disc 205a. As compared to the baffles 126 of FIGS. 10A and 10B, the baffles 226 of FIGS. 12A and 12B may have a differing thickness-to-length ratio. Any size of baffle of any geometry is within the scope of this disclosure.

Further, the proximal end 224 of the mixing disc 205a may be shaped such that bubbles disposed proximal of the mixing disc 205a float to a cavity 212 defining part of a fluid flow path through the mixing disc 205a when mixing disc 205a is disposed within a vertical syringe. This shape may be configured to facilitate de-bubbling of a syringe. As compared to the cavity 112 of FIG. 8, the cavity 212 may be relatively larger with respect to the mixing syringe 205a.

Again, while certain examples above may focus on embolization, the present disclosure is relevant to any application comprising mixing any two components, including two liquids.

Any of the embodiments disclosed above may be used in connection with a variety of procedures. Referring again to FIG. 6, in one exemplary procedure, the tube 104 may be disposed in a mixing bowl or other reservoir where the ingredients are mixed together. For example, a mixing bowl may contain both a liquid 106 and particles 107 configured for use in embolization. The mixing bowl may be configured to prevent the particles 107 from settling within the bowl. The mixture may then be drawn into the syringe 101 by displacing the plunger 102 in a proximal direction to fill the syringe 101. After filling, the syringe 101 may be held vertically to help trapped air escape from the syringe 101, and plunger 102 may be moved to expel any additional air. Next, the tube 104 may be moved to a catheter or needle being used for the intended procedure. As the plunger 102 is displaced distally, the mixing syringe 101 may create a mixing or turbulent flow that tends to mix the particles 107 and the liquid 106 as these elements are ejected from the mixing syringe 101.

In some embodiments, the density of particles 107 may be configured to match the density of the liquid 106. In some embodiments, the liquid may comprise a saline solution with a density of greater than 1, for example. In instances wherein the materials used to make the particles 107 (for example, plastic, glass or ceramic) have a density greater than the suspending component of the mixture, for example, the liquid 106, the particles may comprise hollow particles in order to match densities. Small hollow spheres, known as micro-balloons, including those comprised of polymers and glasses, are commercially available. One supplier is Henkel (http://www.henkelna.com/cps/rde/xchg/henkel_us/hs.xsl/brands-1556.htm?iname=Dualite%25C2%25AE&country-Code=us&BU=industrial&parentredDotUID=0000000-GFR&redDotUID=0000000GFR&brand=000000QTQE).

Matching the densities of the particles and the liquids may create a mixture in which the particles do not quickly settle or accumulate. It is within the scope of this disclosure to utilize particles (such as micro-balloon-shaped polymer or glass spheres) with a density matched to a solution (such as saline) with a mixing syringe as disclosed in any embodiment above. It is also within the scope of this disclosure to dispense such particles from a standard syringe.

Figure 13A:
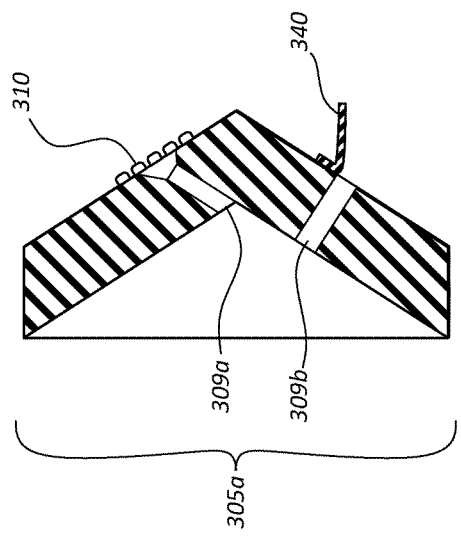
FIG. 13A is a cross-sectional view of a mixing disc according to another embodiment, the mixing disc in a first configuration.
Figure 13B:
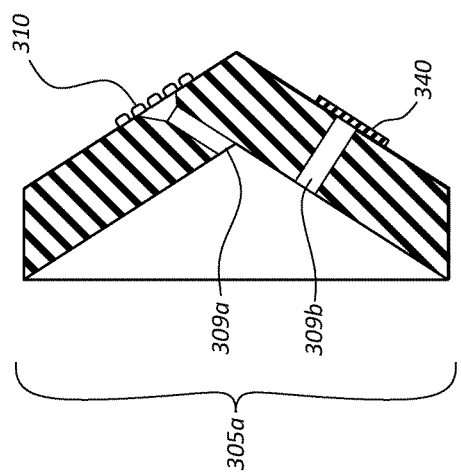
FIG. 13B is a cross-sectional view of the mixing disc of FIG. 13A, the mixing disc in a second configuration.

In some embodiments, more than one passageway may extend through a mixing disc. For example, FIGS. 13A and 13B depict, in two configurations, a first passageway 309a and a second passageway 309b that extend through a mixing disc 305a. The mixing disc 305 may resemble the mixing disc 5a of FIG. 1 in some respects.

The first passageway 309a and the second passageway 309b may be oriented in any suitable orientation relative to each other and/or to the longitudinal axis of the syringe. For example, in some embodiments, the first passageway and second passageway are parallel to each other. In other embodiments, the first passageway 309a and second passageway 309b are not parallel to each other. Further, in some embodiments, one (and only one) of the first passageway and the second passageway is parallel to and/or concentric with the longitudinal axis of the syringe. In other embodiments, neither the first passageway 309a nor the second passageway 309b is parallel to the longitudinal axis of the syringe. One of ordinary skill in the art with the benefit of this disclosure will understand that other suitable orientations of the passageways are possible and/or may be described with reference to other components of a syringe assembly. Such orientations are to be considered within the scope of this disclosure.

One or both of the first 309a and second 309b passageways may be associated with additional features such as valves, screens, porous members, and so forth. For example, in the illustrated embodiment, a porous member 310, such as a filter or screen, is coupled to the second passageway 309a, and a one-way valve 340 is coupled to the second passageway 309b.

In some exemplary embodiments, a mixing disc 305a comprising a first passageway 309a and a second passageway 309b may further comprise or be coupled to a porous member 310 (e.g., a filter, screen, etc.) that prevents solid particles from traversing the first passageway 309a, while lacking an analogous porous member that is associated with the second passageway 309b. In some of these embodiments, the mixing disc 305a may be configured such that retraction of a plunger within the syringe body causes fluid to pass through the first passageway 309a and the porous member 310 associated with the first passageway 309a, but not the second passageway 309b. The second passageway 309b may be controlled by a one-way valve 340 that allows fluid to pass from a proximal side of the mixing disc 305a through the second passageway 309b to a distal side of the mixing disc 305a, but prevents fluid from passing from the distal side of the mixing disc 305a through the second passageway 309b to the proximal side of the mixing disc 305a. Thus, in such an embodiment, no fluid passes through the second passageway 309b as the plunger is retracted within the syringe body. Instead, fluid flows across the mixing disc 305a through a passageway other than the second passageway 309b (e.g., the first passageway 309a) as the plunger is retracted. Upon subsequent advancement of the plunger, fluid may pass through the second passageway 309b. In other embodiments, the one-way valve allows fluid to pass from the distal side of a mixing disc to the proximal side of the mixing disc, but not vice versa.

Any suitable one-way valve 340 may be used in connection with the embodiments described above. For example, a nonporous flap 340 may be coupled to the mixing disc 305a such that a first end of the flap 340 is attached to the mixing disc 305a and a second end of the flap 340 is free to swing away from and toward a passageway (e.g., passageway 309b). Such a flap 340 may occlude the passageway 309b as a plunger is retracted and be pushed away from the passageway 309b as the plunger is advanced, thereby allowing fluid flow only from the proximal side of the mixing disc 305a to the distal side of the mixing disc 305a. One of ordinary skill in the art with the benefit of this disclosure will recognize that other suitable one-way valves (e.g., check valves) may be used. Embodiments comprising such valves are within the scope of this disclosure. Further, as will be recognized by one of ordinary skill in the art with the benefit of this disclosure, other suitable embodiments comprising more than two passageways are possible as well.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A syringe assembly comprising: an elongate syringe body comprising a longitudinal axis; a mixing disc configured to be disposed within the elongate syringe body and displaced along at least a portion of the longitudinal axis of the elongate syringe body in response to a fluidic force; and a first passageway that extends through the mixing disc to connect a first region disposed proximal of the mixing disc with a second region disposed distal of the mixing disc when the mixing discs disposed within the elongate syringe body, wherein a distal end of the first passageway is offset from the longitudinal axis of the elongate syringe body, and wherein a screen is disposed at the distal end of the first passageway, the screen coupled to the mixing disc; and wherein, when the mixing disc is disposed within the elongate syringe body, advancement of liquid through the first passageway generates a liquid vortex in the second region for mixing a plurality of solid particles in a liquid, and wherein the screen is configured to prevent the plurality of solid particles from traversing the first passageway; wherein a diameter of the distal end of the first passageway is greater than a diameter of a proximal end of the first passageway.

2. The syringe assembly of claim 1, wherein a range of displacement of the mixing disc along the longitudinal axis of the elongate syringe body is at least partially limited by a ridge disposed on an internal diameter of the elongate syringe body.

3. The syringe assembly of claim 2, further comprising a plunger including a seal that is configured to move along a movement range within the elongate syringe body, wherein the seal is configured to pass over the ridge such that the movement range of the seal is greater than the range of displacement of the mixing disc, and wherein the movement range of the seal overlaps a portion of the range of displacement of the mixing disc.

4. The syringe assembly of claim 1, wherein at least a portion of the first passageway is positioned parallel to, and offset from, the longitudinal axis of the elongate syringe body.

5. The syringe assembly of claim 1, wherein the first passageway is not parallel to the longitudinal axis of the elongate syringe body.

6. The syringe assembly of claim 1, wherein the first passageway is sized and dimensioned to prevent the plurality of solid particles from traversing the first passageway.

7. The syringe assembly of claim 1, wherein the screen is configured to be displaced by the vortex of liquid as fluid is advanced through the first passageway.

8. The syringe assembly of claim 1, further comprising an anchored string operatively coupled to the mixing disc.

9. The syringe assembly of claim 1, further comprising a second passageway that extends through the mixing disc, wherein fluid flow through the second passageway is controlled by a one-way valve that permits fluid flow from the first region to the second region.

10. The syringe assembly of claim 9, further comprising a plunger that is configured to move longitudinally along the longitudinal axis of the elongate syringe body, wherein the one-way valve comprises a non-porous flap that occludes the second passageway as the plunger is retracted within the syringe body and swings away from the second passageway as the plunger is advanced.

11. The syringe assembly of claim 9, wherein the second passageway is not parallel to the longitudinal axis of the elongate syringe body.

12. The syringe assembly of claim 9, wherein the first passageway is not parallel to the longitudinal axis of the syringe body.

* * * * *

UNITED STATES PATENT AND TRADEMARK OFFICE
CERTIFICATE OF CORRECTION

PATENT NO. : 9,751,056 B2
APPLICATION NO. : 14/283901
DATED : September 5, 2017
INVENTOR(S) : Gregory R. McArthur et al.

It is certified that error appears in the above-identified patent and that said Letters Patent is hereby corrected as shown below:

In the Claims

Column 11, Line 42 Claim 1 reads, ". . . mixing discs disposed within the . . ." which should read, ". . . mixing disc is disposed within the . . ."

Signed and Sealed this
Sixth Day of March, 2018

Andrei Iancu
*Director of the United States Patent and Trademark Office*